United States Patent

Sugden et al.

[11] Patent Number: 5,888,540
[45] Date of Patent: Mar. 30, 1999

[54] PHARMACEUTICAL PRODUCTS

[76] Inventors: Keith Sugden, 27 Outer Trinities, Beverley, North Humberside HU17 0HN, Great Britain; Keith Graeme Hutchison, 8 Coneygar Road, Quenington, Gloucestershire GL7 5BY, Great Britain

[21] Appl. No.: 887,572

[22] Filed: Jul. 3, 1997

Related U.S. Application Data

[63] Continuation of Ser. No. 454,123, Aug. 10, 1995, abandoned, filed as PCT/GB94/02373, Oct. 28, 1994.

[30] Foreign Application Priority Data

Oct. 29, 1993 [GB] United Kingdom .................. 9322314
Jun. 7, 1994 [GB] United Kingdom .................. 9411388

[51] Int. Cl.$^6$ .............................. A61K 9/00; A61K 9/48
[52] U.S. Cl. ......................... 424/455; 424/456; 514/962
[58] Field of Search ..................... 424/455, 456, 424/451, 452; 514/962

[56] References Cited

U.S. PATENT DOCUMENTS

| | | | |
|---|---|---|---|
| 4,126,672 | 11/1978 | Sheth et al. ............ | 424/452 |
| 4,140,755 | 2/1979 | Sheth et al. ............ | 424/464 |
| 4,167,558 | 9/1979 | Sheth et al. ............ | 424/464 |
| 4,255,413 | 3/1981 | Rattie et al. ............ | 424/452 |
| 4,424,235 | 1/1984 | Sheth et al. ............ | 514/567 |
| 4,795,642 | 1/1989 | Cohen et al. ............ | 424/455 |
| 4,935,243 | 6/1990 | Borkan et al. ............ | 424/455 |
| 5,456,918 | 10/1995 | Quirk et al. ............ | 424/451 |

FOREIGN PATENT DOCUMENTS

| | | |
|---|---|---|
| 1546448 | 5/1979 | United Kingdom . |
| 2105590 | 3/1983 | United Kingdom . |
| 2222772 | 3/1990 | United Kingdom . |

OTHER PUBLICATIONS

International Search Report for PCT/GB/02373.

*Primary Examiner*—Robert H. Harrison
*Attorney, Agent, or Firm*—Wallenstein & Wagner, Ltd.

[57] ABSTRACT

A pharmaceutical product in the form of a gelatin capsule with a fill comprises a hydrogel material, a gas generator and an oil-based or hydrophilic based liquid vehicle, wherein upon contact with acidic aqueous medium the gelatin capsule breaks up, disperses or dissolves and the fill reacts to form a foam.

21 Claims, No Drawings

PHARMACEUTICAL PRODUCTS

This present application is a continuation of application Ser. No. 08/454,123 filed Aug. 10, 1995, now abandoned, which was the National Stage of International application Ser. No. PCT/GB94/02373, filed Oct. 28, 1994.

This invention relates to pharmaceutical products and to their preparation. In particular, the invention relates to encapsulated products which are capable of generating a foam when contacted with water.

It is known to treat reflux oesphagitis by administration of a preparation which on contact with gastric acid generates a carbonated gelatinous foam or raft which floats on the stomach contents. When reflux occurs it is this raft which precedes the stomach contents into the oesophagus thus protecting the mucosa from further irritation. Known preparations of this type include solid preparation in the form of powders or tablets containing alginic acid, sodium bicarbonate and antacid materials or liquid preparations containing sodium alginate, sodium bicarbonate and calcium carbonate marketed under the name GAVISCON (TM Reckitt & Colman Products Ltd). British Patent No. 1524740 discloses such liquid preparations.

U.S. Pat. No. 4172120 discloses a preparation including cholestyramine which is retained in the stomach for a prolonged period of time and is therefore more effective in binding duodenally refluxed bile. This preparation includes alginic acid and/or sodium alginate together with sodium bicarbonate which on being swallowed react with gastric acid to form a carbonated raft which holds the cholestryamine sufficiently loosely that it is able to absorb bile acid in the stomach.

The carbonated alginic acid raft type of product is further exemplified by ALGICON (Rhone-Poulenc Rorer) described in European Patent No. 0179858 B1 as containing magnesium alginate, potassium bicarbonate, magnesium carbonate and as antacid materials aluminium hydroxide/magnesium carbonate co-dried gel.

It has now been found that foam generating compositions may be confined within a gelatin capsule if the ingredients are dispersed within an oil or hydrophilic liquid vehicle.

Therefore according to the present invention there is provided a pharmaceutical product in the form of a gelatin capsule with a fill comprising a hydrogel material, a gas generator and an oil-based or hydrophilic based liquid vehicle, wherein upon contact with acidic aqueous medium the gelatin capsule breaks up, disperses or dissolves and the fill reacts to form a foam.

The product of the invention may be in the form of soft or hard gelatin capsules which may be chewed or swallowed or simply immersed in an aqueous medium. The ingredients of the fill are adapted to produce a foam upon contact with water, particularly upon contact with acidic, relatively low pH water of the kind present in a human stomach. The preferred gas generator is a bicarbonate e.g., sodium bicarbonate. On contact with acid, sodium bicarbonate reacts to produce carbon dioxide which becomes entrapped in the hydrogel material to form the foam.

The products of the invention have a wide range of uses eg therapeutical treatment, delivery of a food supplement and as a dietary product. The term pharmaceutical product herein is used generically to refer to products for all such uses.

The fill may optionally include one or more active ingredients such as, pharmacologically active compound, food supplements, dietary products or any combination thereof. When a capsule reaches the stomach and ruptures, its contents will be released and a foam formed. Alternatively, a capsule may be bitten in the mouth and subsequently swallowed. The active ingredient, such as a drug, will be incorporated in the foam and gradually leached out in the stomach to produce a local or systematic effect. In a medical application, this process has a number of advantages. Primarily, the release of the drug and its absorption from the foam is gradual, resulting in better absorption of the drug. The absorption is also more consistent, since gastric emptying times are less variable following oral administration of the foam producing product. Less variation in gastric emptying times means that the time taken for the drug to reach the main absorptive region of the upper small intestine is more consistent. This process also provides improved convenience for patients who require concomitant therapy.

Products according to the present invention are particularly useful in the oral administration for the treatment of digestive problems, such as gastro-oesophageal reflux, hiatus hernia and heartburn.

However, the products of the invention are not limited to oral administration and the capsules may be added to acidic aqueous medium to generate a foam which is then topically applied or ingested.

Examples of suitable hydrogels include polyuronic acids, such as alginic acid or its salts; pectins; polyacrylic acids such as Carbomer; modified celluloses such as hydroxypropyl methylcellulose; microbial polysaccharides, such as Xanthan gum; gellan and carageenan. Mixtures may also be used.

A feature of certain hydrogels, particularly polyuronic acids, is that in aqueous solution they undergo intermolecular cross-linking with divalent metal ions. For example, polyuronic acids are block co-polymer molecules consisting of poly-mannuronic and poly-guluronic acid residues. Divalent metal ions such as calcium in solution will bind by hydrogen bonding, between matching chain regions of poly-guluronic acid. In an aqueous medium, it is known that polyuronates, such as alginate, form gels in the presence of dissolved divalent metal ions.

Preferably the hydrogel material is the sodium, potassium, ammonium, magnesium or calcium salt of alginic acid or the propylene glycolesters or mixtures thereof.

It has been found that when the polymeric material is alginic acid or a salt of ester thereof foams or rafts of higher strength are obtained if the composition includes a source of divalent calcium or trivalent aluminium ion which act as cross-linking agents Suitable sources of calcium ions are those derived from the carbonate, lactate, chloride, gluconate, phosphate, hydrogen phosphate, sulphate, tartrate or citrate salts. Suitable sources of aluminium ions are derived from the carbonate, lactate, glycinate or phosphate salts or from aluminium magnesium carbonate hydroxide, magaldrate, aluminium sodium carbonate hydroxide or aluminium sodium silicate. Generally, the relative quantities by weight of the calcium salt or aluminium compound to the alginic acid or alginate calculated as ions are 4 to 120 $Ca^{2+}$ to 500 alginate or 2 to 80 $Al^{3+}$ to 500 alginate respectively.

Suitable gas generators include carbonate or bicarbonate salts, such as, potassium carbonate or bicarbonate, sodium carbonate or bicarbonate, calcium carbonate, sodium glycine carbonate, magnesium carbonate or aluminium carbonate. The carbonate or bicarbonate salt is present in an amount so as to provide an adequate volume of gas (carbon dioxide) to foam the gel produced when the fill contacts the aqueous acidic medium. Generally, the relative quantities by weight of hydrogel material to the carbonate or bicarbonate calculated as ions is 35 to 300 $CO_3^{2-}$ or $HCO_3^-$ to 500 hydrogel material.

It will be understood that the rigidity and thickness of the carbonated foam formed on contact with the aqueous acidic medium may be varied by altering the ratio of carbonate or bicarbonate to the hydrogel material and upon the type of the hydrogel material.

Suitable oil-based liquid vehicles for use in the invention include hydrogenated natural oils, synthetic oils such as polymethylsiloxane (dimethicone), neutral oils such as fractionated coconut oil, mineral oils, triacetin, ethyl oleate, and other natural oils such as: Soyabean Oil; Arachis Oil; Corn Oil; Sesame Oil; Olive Oil; Rapeseed Oil; Sunflower Oil and Safflower Oil. A preferred oil is fractionated coconut oil.

Suitable hydrophilic based liquid vehicles for use in the invention include: Polyethylene Glycols (PEGs), particularly PEG 400 and PEG 600; Glycofurol; Polyglycerols; Propylene Glycol; Ethanol; Glycerol; Transcutol; polysorbate and propylene carbonate. Mixtures of liquid vehicles may also be used.

Surprisingly, it has been found that sodium bicarbonate can be dispersed with a hydrogel in an oil-based vehicle without the oil inhibiting the formation of a foam on contact with water. It is also surprising that interaction between sodium bicarbonate and the aqueous gelatin shell to provoke premature gas formation can be avoided even during long term storage. This is particularly relevant when a soft gelatin capsule is used as at the manufacturing stage the water content of the capsule shell is relatively high; for example 20 to 30% by weight, although the water content falls to about, 5 to 10% by weight during storage. Contact between the sodium bicarbonate and the capsule shell can be largely inhibited by efficient mixing to ensure complete coating of the bicarbonate particle surfaces with the oil-based vehicle. The selection of the particle size of the bicarbonate is also significant. The particle size is relevant to the quality of the foam produced, and particle sizes not exceeding 100 $\mu$m are preferred.

The stability of the suspension of the carbonate and/or bicarbonate may be improved by the addition of a thickening agent. Suitable thickening agents include colloidal silicon dioxide, such as Aerosil, hydrogenated vegetable fats, glycerol monostearate or glycerol palmitate, and high molecular weight polyethylene glycols eg PEG 1500 to PEG 300.

Another preferred additional ingredient in the contents of capsules of the invention is a surfactant. Efficient dispersion of the oily suspension formulation on contact with the aqueous medium can be enhanced by the use of suitable surfactant system. Surfactants can improve the volume and strength of the foam produced, by maximising the contact with water and allowing the maximum amount of gas to be entrapped. They also increase the opportunity for divalent metal ions to interact with the hydrogel. Suitable surfactants include:

Reaction products of natural or hydrogenated vegetable oils and ethylene glycol; i.e. polyoxyethylene glycolated natural or hydrogenated vegetable oils; e.g. of the type available under the Trade Names CREMOPHOR and NIKKOL;

Polyeoxyethylene-sorbitan-fatty acid esters; e.g. mono- and tri-lauryl, palmityl, stearyl and oleyl esters; e.g. of the type available under the Trade Name TWEEN;

Polyoxyethylene fatty acid esters; e.g. polyoxyethylene stearic acid esters of the type available under the Trade Name MYRJ; Polyoxyethylene-polyoxypropylene co-polymers; e.g. of the type available under the Trade Names PLURONIC and EMKALYX;

Polyoxyethylene-polyoxypropylene block co-polymers; e.g. of the type available under the Trade Name POLOXAMER;

Dioctylsuccinate, dioctylsodiumsulfosuccinate, di-(2-ethylhexyl)-succinate or sodium lauryl sulfate;

Phospholipids, in particular lecithins;

Propylene glycol mono- and di-fatty acid esters such as propylene glycol dicaprylate; propylene glycol dilaurate, propylene glycol hydroxystearate, propylene glycol isostearate, propylene glycol laurate, propylene glycol ricinoleate, and propylene glycol stearate, most preferably propylene glycol caprylic-capric acid diester as is available under the Trade Name MIGLYOL 840; Bile salts, e.g. alkali metal salts such as sodium taurocholate;

Trans-esterification products of natural vegetable oil triglycerides and polyalkylene polyols (e.g. LABRAFIL);

Mono-, di- and mono/di-glycerides, especially esterification products of caprylic or capric acid with glycerol; e.g. of the type available under the Trade Name IMWITOR;

Sorbitan fatty acid esters e.g. of the type available under the Trade Name SPAN, including sorbitan-monolauryl, -monopalmityl, -monostearyl, -tristearyl, -monooleyl and trioleyl esters; Monoglycerides,.e.g. glycerol monooleate, glycerol monopalmitate and glycerol monostearate, for example of the type available under the Trade Names MYVATEX, MYVAPLEX and MYVEROL, and acetylated, e.g. mono- and di-acetylated monoglycerides, for example those available under the Trade Name MYVACET;

Glycerol triacetate or (1,2,3)-triacetin.

Capsules of the invention can include flavouring and aromatic components, in the fill and/or in the capsule shell material itself. Suitable components include essential oils such as lemon, orange and peppermint oils; fruit flavours; aniseed; liquorice; caramel; honey; cream; various spices and combinations of these and other flavours. Such components are supplied by International Flavours & Fragrances, IFF (GB) Ltd. of Haverhill, Suffolk, CB9 8LG ENGLAND.

Natural or artificial sweeteners can also be used, such as; Aspartame, Saccharin, Acesulphame K, Neohesperidine hydrochloride, Mannitol, Xylitol, and Maltitol;

Taste-masking ingredients such as ion exchange resins, cyclodextrins and adsorbates may also be used.

The gelatin capsules may be simultaneously formed and filled using conventional methods and apparatus such as disclosed, for example, in an article by H. Seager in Pharmaceutical Technology September 1985.

The fill is generally prepared by admixing the hydrogel material and gas generator with the liquid vehicle. The thickener is generally added after the initial admixture.

A high speed mixer or colloidal mill is preferably used to ensure a thorough dispersion is obtained. Heating may be employed when necessary.

The encapsulation machine is suitably an R. P. Scherer encapsulation machine.

The invention will now be illustrated by the following Examples.

EXAMPLE 1

A basic formulation for the contents of a soft gelatin capsule embodying the present invention is as follows

|  | Quantity per Capsule |
|---|---|
| Sodium Alginate | 500 mg |
| Calcium Carbonate | 160 mg |
| Sodium Bicarbonate | 270 mg |
| Fractionated Coconut Oil | 580 mg |

On addition of this formulation to an acidic aqueous medium a foam is produced which floats on the surface. The foam is uniformly distributed on the surface and is stable for a substantial period. This formulation can be used as the basis for a therapeutic, pharmaceutical or dietary product, although the proportions may well have to be adjusted to accommodate the additional ingredient or ingredients.

EXAMPLE 2

Fill Formulation:

|  | Quantity per Capsule |
|---|---|
| Alginic Acid | 500 mg |
| Sodium Bicarbonate | 540 mg |
| Calcium Carbonate | 308 mg |
| Fractionated Coconut Oil | 603 mg |
| Lecithin, light | 12 mg |

EXAMPLE 3

| Fill Formulation: | Quantity per Capsule |
|---|---|
| Alginic Acid | 500 mg |
| Sodium Bicarbonate | 250 mg |
| Calcium Carbonate | 408 mg |
| Fractionated Coconut Oil | 743 mg |
| Lecithin, light | 15 mg |
| Colloidal Silicon Dioxide * | 34 mg |
| Sorbitan Fatty Acid Esters ** | 34 mg |
| Polysorbate 80 *** | 18 mg |

* Aerosil 300
** Span 80
*** Tween 80

EXAMPLE 4

| Fill Formulation: | Quantity per Capsule |
|---|---|
| Sodium Alginate | 500 mg |
| Calcium Carbonate | 800 mg |
| Sodium Bicarbonate | 400 mg |
| Fractionated Coconut Oil | 594 mg |
| Lecithin | 12 mg |
| Carbomer | 3 mg |
| Sorbitan Fatty Acid Esters (Span 80) | 34 mg |
| Polysorbate 80 | 18 mg |

EXAMPLE 5

| Fill Formulation: | Quantity per Capsule |
|---|---|
| Sodium Alginate | 500 mg |
| Calcium Carbonate | 800 mg |
| Sodium Bicarbonate | 400 mg |
| Fractionated Coconut Oil | 594 mg |
| Lecithin | 12 mg |
| Colloidal Silicon Dioxide (Aerosil) | 34 mg |
| Sorbitan Fatty Acid Esters (Span 80) | 34 mg |
| Polysorbate 80 | 18 mg |

EXAMPLE 6

Capsules in a standard gelatine shell were prepared having the following fill weights:

| Fill Formulation |  |
|---|---|
| Sodium Alginate | 500 mg |
| Sodium Bicarbonate BP | 100 mg |
| Calcium Carbonate | 30 mg |
| Fractionated Coconut Oil | 600 mg |
| Lecithin | 12 mg |
| Colloidal Silicon Dioxide | 34 mg |
| Sorbitan Fatty Acid Esters | 34 mg |
| Polysorbate 80 | 20 mg |
| Flavouring, colouring, sweetener | 80 mg |

EXAMPLE 7

Capsules were prepared as in Example 6 except the amount of calcium carbonate in the fill formulation was increased to 100 mg.

EXAMPLE 8

Capsules were prepared as in Example 6 having the following fill:

|  | Quantity/Capsule |
|---|---|
| Sodium Alginate | 500 mg |
| Xantham Gum | 100 mg |
| Sodium Bicarbonate | 100 mg |
| Calcium Carbonate | 100 mg |
| Aerosil | 35 mg |
| Flavour, Sweetener | qs |
| Soya Bean Oil | qs ad |
|  | 1500 mg |

EXAMPLE 9

Capsules were prepared as in Example 6 having the following fill:

|  | Quantity/Capsule |
|---|---|
| Alginic Acid | 500 mg |
| Carrageenan | 100 mg |
| Sodium Carbonate | 100 mg |
| Calcium Chloride | 100 mg |
| Aerosil | 35 mg |
| Polysorbate 80 | 20 mg |

-continued

| | Quantity/Capsule |
|---|---|
| Flavour, Sweetener | qs |
| Fractionated Coconut Oil | qs ad |
| | 1500 mg |

EXAMPLE 10

Capsules were prepared as in Example 6 having the following fill:

| | Quantity/Capsule |
|---|---|
| Magnesium Alginate | 500 mg |
| Gellan Gum | 50 mg |
| Magaldrate | 200 mg |
| Sodium Bicarbonate | 150 mg |
| Glyceryl Mono-Stearate | 100 mg |
| Polysorbate 80 | 20 mg |
| Flavour, Sweetener | qs |
| Fractionated Coconut Oil | qs ad |
| | 1600 mg |

EXAMPLE 11

Capsules were prepared as in Example 6 having the following fill:

| | Quantity/Capsule |
|---|---|
| Alginic Acid | 300 mg |
| Pectin | 300 mg |
| Calcium Carbonate | 150 mg |
| Sodium Bicarbonate | 150 mg |
| Hydrogenated Vegetable Oil | 150 mg |
| Lecithin | 15 mg |
| Flavour, Sweetener | qs |
| Arachis Oil | qs ad |
| | 1550 mg |

We claim:

1. A pharmaceutical product in the form of a soft gelatin capsule with a fill comprising a hydrogel material, a gas generator, and an oil-based vehicle, the gas generator comprising a mixture of a carbonate and a bicarbonate having a particle size not exceeding 100 $\mu$m which is suspended in said oil-based liquid vehicle, wherein upon contact with acidic aqueous medium the soft gelatin capsule breaks up, disperses or dissolves and the fill reacts to form a foam.

2. A product as claimed in claim 1 in which the hydrogel material is selected from the group consisting of polyuronic acids; pectins; polyacrylic acids; modified cellulose and microbial polysaccharides.

3. A product as claimed in claim 1 or claim 2 in which the hydrogel material is selected from alginic acid, alginates, pectin, xanthan, gellan, carageenan and mixtures thereof.

4. A product as claimed in claim 3 wherein the hydrogel material is alginic acid or the alginates, is the sodium, potassium, ammonium, magnesium or calcium salts or the propylene glycol esters or mixtures thereof.

5. A product as claimed in claim 3 which includes a calcium or aluminum cross-linking ion.

6. A product as claimed in claim 5 wherein the calcium ion is derived from the carbonate, lactate, chloride, gluconate, phosphate, hydrogen phosphate, sulphate, tartrate or citrate salt.

7. A product as claimed in claim 5 wherein the aluminum ion is derived from the carbonate, lactate, glycinate or phosphate salt or from, aluminum magnesium carbonate hydroxide, magaldrate, aluminum sodium carbonate hydroxide or aluminum sodium silicate.

8. A product as claimed in claim 1 in which the carbonate or bicarbonate is potassium carbonate or bicarbonate, sodium carbonate or bicarbonate, calcium carbonate, sodium glycine carbonate, magnesium carbonate or aluminum carbonate.

9. A product as claimed in claim 1 in which the oil-based or hydrophilic based liquid vehicle is fractionated coconut oil, polyethylene glycol, propylene glycol or triglycerides.

10. A product as claimed in claim 1 in which the fill includes a surfactant.

11. A product as claimed in claim 1 in which the fill includes a thickening agent.

12. A product as claimed in claim 11 in which the thickening agent is colloidal silicon dioxide.

13. A product as claimed in claim 1 in which the fill includes a pharmacologically active compound, a food supplement and/or a dietary product.

14. A product as claimed in claim 1 further having a carbonate-to-bicarbonate weight ratio of 16:27.

15. A product as claimed in claim 1 further having a carbonate-to-bicarbonate weight ratio of 154:270.

16. A product as claimed in claim 1 further having a carbonate-to-bicarbonate weight ratio of 204:125.

17. A product as claimed in claim 1 further having a carbonate-to-bicarbonate weight ratio of 2:1.

18. A product as claimed in claim 1 further having a carbonate-to-bicarbonate weight ratio of 3:10.

19. A product as claimed in claim 1 further having a carbonate-to-bicarbonate weight ratio of 1:1.

20. A pharmaceutical product in the form of a soft gelatin capsule with a fill comprising a hydrogel material, a surfactant a gas generator, and an oil-based liquid vehicle, the gas generator comprising a mixture of a carbonate and a bicarbonate having a particle size not exceeding 100 $\mu$m which is suspended in said oil-based liquid vehicle, wherein upon contact with acidic aqueous medium the soft gelatin capsule breaks up, disperses or dissolves and the fill reacts to form a foam.

21. A method of encapsulating a foam forming mixture comprising a hydrogel material and a gas generator, the gas generator comprising a mixture of a carbonate and a bicarbonate having a particle size not exceeding 100 $\mu$m, the method comprising admixing said foam forming mixture with an oil-based liquid vehicle to form a fill formulation and encapsulating the fill formulation in a soft gelatin capsule.

* * * * *

UNITED STATES PATENT AND TRADEMARK OFFICE
CERTIFICATE OF CORRECTION

PATENT NO. : 5,888,540
DATED : March 30, 1999
INVENTOR(S) : Keith Sugden; Keith Graeme Hutchison It is certified that error appears in the above-identified patent and that said Letters Patent is hereby corrected as shown below:

In Column 1, Lines 4-6, replace "now abandoned, which was the National Stage of International Application Ser. No. PCT/GB94/02373, filed Oct. 28, 1994" with "now abandoned.".

In Column 1, Line 60, replace "eg" with "e.g.".

In Column 3, Line 45, replace "eg" with "e.g.".

In Column 2, Line 41, replace" glycolesters" with "glycol esters".

In Column 7, Line 46, replace "oil-based vehicle" with "oil-based liquid vehicle".

In Column 7, Line 57, replace "from alginic acid" with "from the group consisting of alginic acid".

In Column 8, Lines 44-45, replace "a surfactant a gas generator" with "a surfactant, a gas generator".

Signed and Sealed this

Eleventh Day of April, 2000

Q. TODD DICKINSON

*Attest:*

*Attesting Officer*       *Director of Patents and Trademarks*